United States Patent
Verstege et al.

(10) Patent No.: US 10,238,463 B2
(45) Date of Patent: *Mar. 26, 2019

(54) PROCESSING SYSTEM ARRANGED TO COOPERATE WITH AN OPTICAL-SHAPE-SENSING-ENABLED INTERVENTIONAL DEVICE

(71) Applicant: KONINKLIJKE PHILIPS N.V., Eindhoven (NL)

(72) Inventors: Marco Verstege, Eindhoven (NL); Jeroen Gerard Scheepens, Best (NL); Neriman Nicoletta Kahya, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/510,373

(22) PCT Filed: Sep. 6, 2015

(86) PCT No.: PCT/EP2015/070309
§ 371 (c)(1),
(2) Date: Mar. 10, 2017

(87) PCT Pub. No.: WO2016/041793
PCT Pub. Date: Mar. 24, 2016

(65) Prior Publication Data
US 2017/0281293 A1 Oct. 5, 2017

(30) Foreign Application Priority Data
Sep. 16, 2014 (EP) .................................... 14184869

(51) Int. Cl.
*G06K 9/00* (2006.01)
*A61B 90/00* (2016.01)
(Continued)

(52) U.S. Cl.
CPC .............. *A61B 90/37* (2016.02); *A61B 34/20* (2016.02); *G06T 7/0012* (2013.01); *G06T 7/11* (2017.01);
(Continued)

(58) Field of Classification Search
CPC ... A61B 34/20; A61B 17/00234; A61B 1/018; A61B 2034/2061; A61B 2017/0034; A61B 2017/00469; A61B 90/37
See application file for complete search history.

(56) References Cited

U.S. PATENT DOCUMENTS

| 5,860,923 A | 1/1999 | Lenker |
| 8,467,855 B2 | 6/2013 | Yasui |

(Continued)

FOREIGN PATENT DOCUMENTS

| EP | 2289578 | 3/2011 |
| EP | 2667815 | 12/2013 |

(Continued)

OTHER PUBLICATIONS

Office action on JP application No. 20170512954, dated Nov. 27, 2018. (No translation available.).

*Primary Examiner* — Amir Alavi (57) ABSTRACT

The invention relates to a processing system (200) that is arranged to cooperate with an optical-shape-sensing-enabled elongated interventional device (1020, 1120, 1220, 1320, 1420), such as a catheter comprising an optical fiber. A reconstructed shape data providing unit (130) provides reconstructed shape data for the interventional device (1020, 1120, 1220, 1320, 1420). A virtual marking provider unit (140) provides at least one virtual marking (1020A, 1020B, 1101, 1102, 1103, 1201, 1203, 1204, 1301, 1302, 1401) based on the reconstructed shape data, for example as overlay to a x-ray image. The present invention thus turns (Continued)

any OSS-enabled device into a calibrated device, suitable for all kinds of live 3D measurements.

11 Claims, 8 Drawing Sheets

(51) Int. Cl.
    *A61B 34/20*      (2016.01)
    *G06T 7/11*      (2017.01)
    *G06T 7/00*      (2017.01)
    *A61B 34/00*      (2016.01)

(52) U.S. Cl.
    CPC ....... *A61B 34/25* (2016.02); *A61B 2034/2061* (2016.02); *A61B 2090/061* (2016.02); *A61B 2090/067* (2016.02); *A61B 2090/365* (2016.02); *A61B 2090/376* (2016.02); *G06T 2207/10116* (2013.01)

(56) References Cited

U.S. PATENT DOCUMENTS

| | | |
|---|---|---|
| 9,264,542 B2 | 2/2016 | Stine et al. |
| 9,430,717 B2 | 8/2016 | Denissen |
| 2002/0095265 A1* | 7/2002 | Satoh ............... A63F 13/00 702/94 |
| 2003/0227542 A1* | 12/2003 | Zhang ............... G02B 27/017 348/61 |
| 2009/0143633 A1 | 6/2009 | Edmundson et al. |
| 2009/0182225 A1 | 7/2009 | Foley et al. |
| 2010/0249506 A1 | 9/2010 | Prisco |
| 2010/0318182 A1 | 12/2010 | Qanadli |
| 2011/0160571 A1* | 6/2011 | Cohen .................. A61B 5/06 600/424 |
| 2012/0147028 A1 | 6/2012 | Frisinger |
| 2013/0216025 A1 | 8/2013 | Chan et al. |
| 2013/0308137 A1 | 11/2013 | Manzke et al. |
| 2013/0308138 A1 | 11/2013 | 'T Hooft et al. |
| 2013/0317356 A1 | 11/2013 | Ramachandran et al. |
| 2014/0052241 A1 | 2/2014 | Harks et al. |
| 2014/0135744 A1 | 5/2014 | Stein et al. |
| 2014/0206288 A1 | 7/2014 | Ramachandran et al. |
| 2015/0230730 A1 | 8/2015 | Sabczynski et al. |
| 2016/0000519 A1* | 1/2016 | Dehghan Marvast ...................... A61B 19/5244 600/424 |
| 2016/0228200 A1* | 8/2016 | Denissen ............ A61B 5/065 |
| 2017/0304010 A1* | 10/2017 | Van Der Linde ...... A61B 34/20 |
| 2017/0354346 A1* | 12/2017 | Bharat .................. A61B 5/062 |
| 2017/0368368 A1* | 12/2017 | Bharat ................ A61N 5/1048 |
| 2018/0014889 A1* | 1/2018 | Denissen ............. A61B 34/20 |

FOREIGN PATENT DOCUMENTS

| | | |
|---|---|---|
| JP | 2001070439 A | 3/2017 |
| WO | 2012101562 | 10/2012 |
| WO | 2012147028 | 11/2012 |
| WO | 2013136247 | 9/2013 |
| WO | 2014053925 | 4/2014 |
| WO | 2014053934 A1 | 4/2014 |
| WO | 2014060889 | 4/2014 |

\* cited by examiner

PROCESSING SYSTEM ARRANGED TO COOPERATE WITH AN OPTICAL-SHAPE-SENSING-ENABLED INTERVENTIONAL DEVICE

CROSS-REFERENCE TO PRIOR APPLICATIONS

This application is the U.S. National Phase application under 35 U.S.C. § 371 of International Application Serial No. PCT/EP2015/070309, filed on Sep. 6, 2015, which claims the benefit of European Patent Application No. 14184869.7, filed on Sep. 16, 2014. These applications are hereby incorporated by reference herein.

FIELD OF THE INVENTION

The invention relates to a processing system that is arranged to cooperate with an optical-shape-sensing-enabled interventional device. The invention further relates to an imaging system for imaging an interventional device within a subject. The invention further relates to a processing method. The invention further relates to a processing computer program for providing at least one virtual marking for an optical-shape-sensing-enabled interventional device.

BACKGROUND OF THE INVENTION

US 2010/318182 A1 discloses a sheath for introducing devices such as a stent or other devices, said sheath comprising several reference markers along a predetermined part of said sheath for in situ measuring purposes.

However, each time a measurement is performed, such a dedicated calibrated device needs to be used, because not every interventional device has these reference markers. In endovascular procedures, when a guide wire is in place, one option is to slide a calibrated device over the guide wire, but such an operation requires some tedious work replacing devices.

SUMMARY OF THE INVENTION

It is an object of the present invention to provide an improved processing system that is arranged to cooperate with an optical-shape-sensing-enabled interventional device, an improved imaging system for imaging an interventional device within a subject, an improved processing method, and an improved processing computer program for providing at least one virtual marking for an optical-shape-sensing-enabled interventional device, which overcome the need for dedicated devices to perform measurements and which do not require unnecessary replacement work.

In a first aspect of the present invention, there is provided a processing system, wherein said processing system is arranged to cooperate with an optical-shape-sensing-enabled elongated interventional device, wherein said interventional device is configured for being arranged within a subject; wherein said processing system comprises: a reconstructed shape data providing unit that is configured for providing reconstructed shape data of said interventional device; and a virtual marking provider unit that is configured to provide at least one virtual marking based on said reconstructed shape data.

The first aspect of the present invention relates to a system, with which a conventional OSS-enabled interventional device may be turned into a "virtual" calibrated device, such as, e.g., a physical medical device. The device thus does not need to contain any radiopaque markers, in contrast to prior-art devices. The present invention can be used for any OSS-enabled device (i.e., for any device with integrated optical shape sensing). By means of the present invention, it is possible to perform measurements without doing an image registration. The reconstructed shape data provided by the reconstructed shape data providing unit may be, e.g., a set of coordinates defined in this coordinate system (which is typically in metric space). A user can measure for example the length of a blood vessel by looking at the curves in the shape of the device. At the point where the interventional device enters or exits the vessel there might be a bend, so the device length between two bends, or between a bend and the device tip, gives lots of information to the user. As explained below, the present invention supports providing visual information about these distances, for example by showing a ruler along the device.

Optical shape sensing (OSS) technology generally relates to tracking the shape (i.e., individual positions and/or locations) of an optical fiber along at least a part of its length, preferably along its entire length. An OSS-enabled fiber can be used to monitor a three-dimensional shape of an object into which the fiber may be embedded or introduced. An example description of three-dimensional shape reconstruction of an optical fiber embedded within an elongated device may be found in US 2013/308138 A1 which is incorporated herein by reference. Optical shape sensing typically uses a multi-core optical fiber to reconstruct a shape along the length of a device. The present invention supports providing a virtual representation of an interventional device, for example as overlay on top of x-ray. The way the interventional device is represented is independent of the actual type of interventional device, thus, the representation can be a polyline, a tube, or a mesh. The present invention thus turns any regular OSS-enabled device into a calibrated device, which is suitable for various kinds of live 3D measurements.

An interventional device may comprise, e.g., an (ultrasound) probe, an endoscope, a needle or a catheter including, but not limited to diagnostic angiographic catheters, micro catheters, drainage catheters, balloon catheters, and central venous catheters.

When referring to an OSS-enabled interventional device, reference is typically made to an interventional device which is configured to provide data to be used for performing optical shape sensing. To that extent, the interventional device preferably comprises at least one optical fiber. Although the first aspect relates to an "elongated" interventional device, it is noted that as long as a known part of an optical fiber is connected to a rigid (part of a) device and the model of that device (part) is known, it is possible to virtually reconstruct and track it in space.

A subject may e.g. refer to a living organism such as a human or animal being.

Having tracked the shape (i.e., individual positions and/or locations) of the interventional device by means of optical shape sensing, an optical shape sensing unit acquires a wealth of data, referred to herein as "optical shape sensing data".

As explained above, optical shape sensing (OSS) technology generally relates to tracking the shape of an optical fiber along at least a part of its length, preferably along its entire length. Herein, OSS technology is employed for tracking the shape of the interventional device along at least a part of its length, preferably along its entire length.

When referring to "shape reconstruction", one typically refers to capturing the shape and appearance of an object. This may involve providing a three-dimensional parameterization of the object, i.e., coordinates in metric 3D space. Shape reconstruction in optical shape sensing typically starts from a reconstruction launch point, i.e., some point along the optical fiber where the reconstruction starts. This point is usually chosen as the origin of the OSS coordinate system.

It is generally known, e.g., from WO2012101562A1, EP2667815A2, WO2014053934A1, or WO2014053925A1 how the reconstructed shape data may be provided, how the three-dimensional parameterisation of an object is implemented, and how the reconstruction launch point is determined.

WO2012101562A1, which is incorporated herein by reference, discloses an optical shape sensing system employing an elongated device, an optical fiber embedded within the elongated device with the optical fiber including one or more cores, an optical interrogation console and a 3D shape reconstructor. In operation, the optical interrogation console generates reflection spectrum data indicative of a measurement of both an amplitude and a phase of a reflection for each core of the optical fiber as a function of wavelength and the 3D shape reconstructor reconstructs a 3D shape of the optical fiber. The 3D shape reconstructor executes a generation of local strain data for a plurality of positions along the optical fiber responsive to the reflection spectrum data, a generation of local curvature and torsion angle data as a function of each local strain along the fiber, and a reconstruction of the 3D shape of the optical fiber as a function of each local curvature and torsion angle along the optical fiber.

EP2667815A2, which is incorporated herein by reference, discloses an integrated optical shape sensing system and method including an arrangement structure configured to receive a fiber port or connector. A platform is configured to provide a distance relationship with the arrangement structure such that the fiber port or connector is trackable to provide a location reference. The platform secures a patient in proximity to the arrangement structure. An optical shape sensing enabled interventional instrument has a first optical fiber cable connectable to the fiber port or connector. An optical interrogation module is configured to collect optical feedback from the instrument and has a second optical fiber cable connectable to the fiber port or connector such that a known reference position is provided for accurate shape reconstruction.

WO2014053934A1, which is incorporated herein by reference, discloses registering the measurement signals of an optical fiber shape sensor with the imaging plane of an imaging device that images the fiber shape sensor. A reference plane of the imaging device is referenced to a reference plane of the fiber shape sensor such that the measurement error originating from the fiber birefringence is minimized for that plane.

WO2014053925A1, which is incorporated herein by reference, discloses a system and method for registering a coordinate system for a shape sensing system to a coordinate system for pre-procedural or intra-procedural imaging data. A stable curvature in a shape reconstruction is identified and matched to another curvature, where the other curvature is from another shape construction from a subsequent time or from imaging data from another imaging modality. The matched curvatures are aligned, aligning the coordinate systems for the respective curvatures.

The launch point may be, e.g., a calibrated point along the fiber that is kept static in a known space (e.g., a fixed position relative to an operating table, which is in a known space when the x-ray system has table tracking).

Prior-art calibrated interventional devices make use of reference markers such as radiopaque markers to employ the fact that the positions of the markers on the device (and therefore distances inside the patient) are known. A radiopaque marker typically comprises a radiopaque material, i.e., a material through which electromagnetic radiation (such as, e.g., x-rays) is relatively unable to pass. In contrast, the present invention employs "virtual markings". A virtual marking may refer to a location positioned along the reconstructed shape of the interventional device. The term "virtual" is used herein to express that the markings do not physically exist as such but are made to appear to do so by, e.g., software being employed by the virtual marking provider unit.

An at least one virtual marking, e.g., in the form of a ruler (such as, e.g., most prior-art devices), may be provided by interpolating over the provided shape (which is an array of three-dimensional points with known relative distances). Also, the tip of a device can function as a sort of three-dimensional cursor. In particular, the location of the tip can be used to mark the coordinate at a certain point of time. Furthermore, a user may add virtual markers in pre-operative data such as CT or MR which can be registered to OSS devices.

The reconstructed shape data providing unit may comprise an input unit such that the processing system is configured for receiving reconstructed shape data of an interventional device via the input unit. The reconstructed shape data providing unit may also provide reconstructed shape data by accessing an internal or external storage medium. The reconstructed shape data providing unit may also comprise a shape reconstruction unit that is configured to perform a shape reconstruction step on optical-shape-sensing data provided thereto. The reconstructed shape data providing unit may be configured to receive data via physical means, such as, e.g., a data cable plugged into the input unit. The reconstructed shape data providing unit may additionally and/or alternatively be configured to receive data via non-physical means, such as by means of a wireless connection. The reconstructed shape data providing unit may additionally and/or alternatively comprise storage means configured to store reconstructed shape data.

Registering pre-operative medical data to a patient on an operating table via an x-ray system is known inter alia from, e.g., WO2012101562A1, EP2667815A2, WO2014053934A1, or WO2014053925A1, which describe some sort of registration of OSS to an imaging modality like x-ray. Therefore, a direct mapping is provided between the coordinate system of pre-op data, the patient, x-ray system and OSS. Markers placed in a correctly-registered CT scan can therefore easily be converted to positions in the OSS space and used for measurements.

Typically, some sort of calibration and registration would be desirable for the x-ray system and the OSS system setup to get a correct mapping between these spaces. However, when only the OSS space is considered and the user can see that a shape of a device is following a certain anatomy, the user can use the ruler function without any registration to measure the distance between two branches, for instance.

In an embodiment, said interventional device comprises at least one optical fiber.

In a further embodiment, the interventional device comprises at least one optical fiber, and the optical fiber comprises a reconstruction launch point.

In a further embodiment, the interventional device comprises at least one optical fiber, and the interventional device comprises an elongated device, wherein said optical fiber is embedded within said interventional device.

In a further embodiment, the at least one virtual marking comprises reference coordinates.

In a further embodiment, the at least one virtual marking comprises metadata providing information on said at least one virtual marking. The metadata may involve, e.g., a label or reference identification number of the virtual marking. The metadata may additionally and/or alternatively involve one or more labels on a ruler indicating a distance information. The metadata may additionally and/or alternatively involve one or more customized labels, for example to mark a point of interest. Accordingly, a user is provided with a straightforward and easy-to-use way to differentiate one virtual marking from another, without e.g., having to count the virtual markings.

In a further embodiment, the processing system comprises an output configured to provide said reconstructed shape data and said at least one virtual marking. By means of the output of the processing system, it is possible to store said reconstructed shape data and said at least one virtual marking on a storage medium. That way, said reconstructed shape data and said at least one virtual marking may be processed further at a later stage.

In a further embodiment, the processing system further comprises a region of interest representation unit that is configured for generating a region of interest representation representing a region of interest within said subject; and a registration unit that is configured to register said at least one virtual marking when said interventional device is arranged within said subject with said region of interest representation.

In an embodiment, the processing system is configured to determine a distance between said at least one virtual marking and a reference point. The reference point may be a reference coordinate in the vicinity of the interventional device. The reference point may also be a marked point in a CT or MR image. The reference point may also be a point provided by an EM device. Further, the processing system may be configured to determine a distance between said at least one virtual marking and a centerline of a segmented vessel. Further, the processing system may be configured to determine a distance between said at least one virtual marking and (segmented) anatomical features such as calcification, Ostia and/or a vessel wall. Further, the processing system may be configured to determine a distance between said at least one virtual marking and an intersection point with a plane. Further, the processing system can determine a cut plane of a volume. In this plane, 2D measurements may be performed, such as determining an area (of a vessel's outline) and of a shortest distance to a vessel wall. Preferably, the embodiment comprises performing a registration.

The distance may refer to a Euclidean shortest distance between the first and second virtual marking. Or, the distance may refer to a distance along a predefined curve. Or, the distance may refer to the shortest distance along a predefined surface, wherein the surface is a two-dimensional surface in three-dimensional space, and wherein the surface includes the first and second virtual marking. For instance, the length of the path that the tip (or any other particular point) of the device traveled during a certain period of time might be useful for the user. Further, if one device is in the lumen of the other, for example a guide wire inside a catheter, the distance along the device from one distal tip to the distal tip of the other device is useful information, because the user will learn how far a device can be inserted before the tips reach each other. It can further be used to do quick length measurements, e.g., by holding each tip at one end of a lesion so that the distance between both tips reveals information on the size of the lesion. Other applications involve a live distance measurement between (user-defined) fixed points on multiple devices, independent of whether they are inside each other or not. Also, the distance between a defined 3D location (landmark) and a fixed position on a device may be determined. As noted above, a user may be interested in the shortest distance between a defined 3D location (landmark) and a device.

A user may also choose to arrange two-dimensional landmarks on x-ray images and use those for distance measurements in combination with a device, where distance measurements may be, e.g., the shortest distance or the distance to a point on the shape. The two-dimensional landmark may describe a line in three dimensions from the source of the x-ray system to the detector. Quite frequently, the distance is not the exact distance between the anatomical feature tagged with the 2D landmark and the device, because it is not known where the anatomical feature is positioned on the line. There are different options to provide the user with a distance, which is some sort of estimation of the real distance. For instance, the position on the line has the same depth as the position on the device, so the measurement is in the plane perpendicular to the x-ray image. Alternatively, a position is chosen on the line in the plane which goes through the iso-center and is perpendicular to the x-ray image. Further, a user may choose to determine the depth, for example with help of an image made from a different angle.

In a further embodiment, the virtual marking provider unit is configured to provide a first and a second virtual marking, wherein said processing system is configured to determine a distance between said first and second virtual markings.

In a further embodiment, the virtual marking provider unit is configured to provide a first, second, and third virtual marking, wherein said processing system is further configured to determine at least one angle formed by said first, second, and third virtual markings.

In a further embodiment, the virtual marking provider unit is configured to provide a plurality of triples of virtual markings, wherein said processing system is further configured to determine at least one angle for at least one of said triples of virtual marking.

In a further embodiment, the virtual marking provider unit is configured to provide a first pair and a second pair of virtual markings, wherein said first pair and said second pair are forming respective first and second straight lines, and wherein said processing system is further configured to determine at least one angle formed by said first and second straight lines.

In a second aspect of the present invention, there is provided an imaging system for imaging an elongated interventional device within a subject, wherein said imaging system comprises the processing system and a display unit that is configured to display said at least one virtual marking.

An imaging system may for instance refer to an x-ray imaging system for imaging a subject, such as, e.g., a patient. Likewise, the imaging system may be a computed tomography apparatus, a magnetic resonance apparatus, an ultrasound apparatus or another imaging modality.

In an embodiment, said imaging system further comprises a region of interest representation unit that is configured for generating a region of interest representation representing a region of interest within said subject; and a registration unit that is configured to register said at least one virtual marking when said interventional device is arranged within said subject with said region of interest representation; wherein said display unit is configured to display said at least one virtual marking together with said region of interest representation.

When referring to a region of interest (ROI) within the subject, the present invention typically relates to the boundaries (in 2D) or the contours or surfaces (in 3D) outlining an object or a volume within the subject.

Herein, the term "representation" may in particular refer to an image, such as, e.g., an x-ray image. Likewise, the image may be a computed tomography image, a magnetic resonance image, an ultrasound image or a three-dimensional image of another imaging modality.

Image registration generally relates to mapping different sets of (typically imaging) data into a single coordinate system. By means of an image registration comparing or integrating data obtained from different measurements is possible. In the context of the present invention, registration typically means that a relation of the shape coordinate system (space) to a certain other space, for example a space defined for an x-ray system (such as, e.g., image space, table space, patient space, detector space, etc.) is known. One option to perform registration would be to keep a reconstruction launch point at a known fixed position in a certain other space (e.g., one may fix the launch region to the table). A "reference marker" would then be the known fixed position (and orientation). By detecting the markers in x-ray, it is possible to perform a mapping between markers in x-ray space and in shape space, i.e., a registration. A registration may also be used to determine distances in an x-ray image.

The display unit may refer to a projector screen, a computer monitor, or other modality configured to graphically represent an image.

Preferably, the scale (unit size) of virtual marking or virtual markings can be adjusted to the preference of the user (e.g., centimeters or millimeters) or the standard in the geographical area (e.g., metric system or imperial system). Accordingly, the present invention may provide for different scales without having to change the physical device. The scale can also be dependent on how far the user zooms in.

In an embodiment, the display unit is configured to receive a toggle-off signal causing said display unit to cease displaying (or to refrain from displaying) said at least one virtual marking; wherein said display unit is further configured to receive a toggle-on signal causing said display unit to display said at least one virtual marking.

In a further embodiment, the display unit is configured to display a three-dimensional (3D) virtual ruler. By providing a 3D virtual ruler instead of only providing the 3D distance between the points, distance information of content visible in the X-ray can be measured more accurately. In a similar way, three 3D points can define a 3D plane, which can be used for a ruler grid, such that measurements can be done in this plane.

In a further embodiment, the display unit is configured to provide a suggested viewing perspective.

A suggested viewing perspective (or viewing position), such as, e.g., a table and C-arm position, may be provided based on the position and shape of the device. A user may also choose to define three points on the reconstructed shape that in turn define a viewing plane. The viewing plane may then be automatically calculated by the processing apparatus based on, e.g., certain points, curvature, direction of certain points or a combination of all these.

In a third aspect of the present invention, there is provided a processing method comprising: providing reconstructed shape data of an optical-shape-sensing-enabled elongated interventional device, wherein said interventional device is configured for being arranged within a subject; and providing at least one virtual marking based on said reconstructed shape data.

In a fourth aspect of the present invention, there is provided a processing computer program for providing at least one virtual marking for an optical-shape-sensing-enabled elongated interventional device, the processing computer program comprising program code means for causing a processing system as defined in claim 1 to carry out the steps of the processing method as defined in claim 10, when the computer program is run on a computer controlling the processing system.

It shall be understood that the processing system of claim 1, the imaging system of claim 7, the processing method of claim 10, and the processing computer program of claim 11 have similar and/or identical preferred embodiments as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
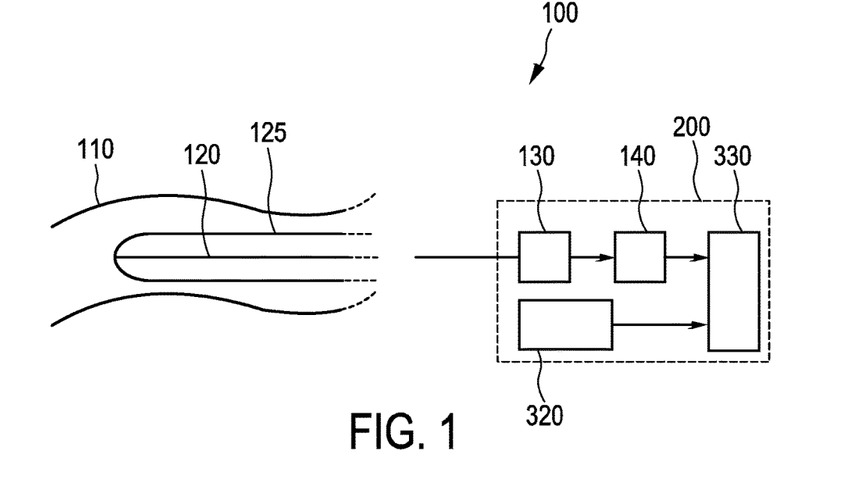
FIG. 1 shows schematically and exemplarily an interventional system comprising an embodiment of a processing system.

FIG. 1 shows schematically and exemplarily an embodiment of an interventional system 100 comprising an optical-shape-sensing-enabled interventional device 125 and a processing system 200. The interventional device 125 is configured for being arranged within a subject 110. The interventional system 100 comprises: an optical shape sensing unit 120 that is configured to provide optical shape sensing data for at least a part of the interventional device 125 by means of an optical fiber embedded within the interventional device 125 and a light source (not shown). The processing system 200 comprises a reconstructed shape data providing unit 130 that is configured to provide reconstructed shape data for the interventional device 125; and a virtual marking provider unit 140 that is configured to provide at least one virtual marking based on said reconstructed shape data. Reconstructed shape data providing unit 130 may comprise a shape reconstruction unit, which performs shape reconstruction to deliver reconstructed shape data. Optical shape sensing unit 120 may comprise, e.g., a light source and an optical fiber. Interventional device 125 may comprise, e.g., an elongated device such as e.g. a catheter. As described in more detail herein below, processing system 200 may further comprise an optional region of interest representation unit 320 that is configured for generating a region of interest representation representing a region of interest within the subject 110. Processing system 200 may further comprise an optional registration unit 330 that is configured to register said at least one virtual marking when said interventional device is arranged within said region of interest within the subject 110 with said region of interest representation.

Figure 2:
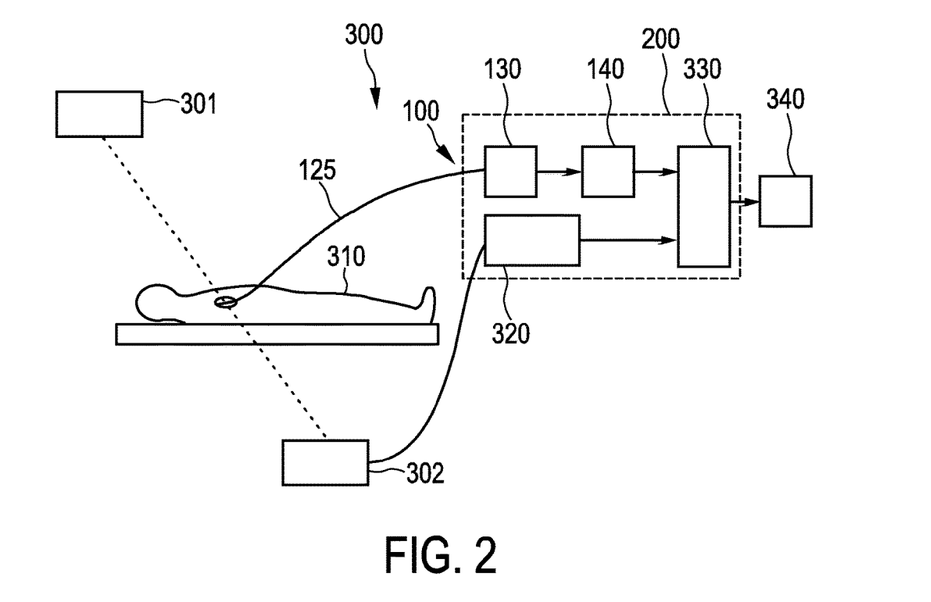
FIG. 2 shows schematically and exemplarily an embodiment of an imaging system.

FIG. 2 shows schematically and exemplarily an embodiment of an imaging system 300 for imaging interventional device 125 of interventional system 100 within a subject 310. Imaging system 300 may e.g. comprise an x-ray imaging system with one or more x-ray sources 301 and one or more x-ray detectors 302. Imaging system 300 comprises: the processing system 200 and a display unit 340 that is configured to display said at least one virtual marking together with said region of interest representation.

Figure 3:
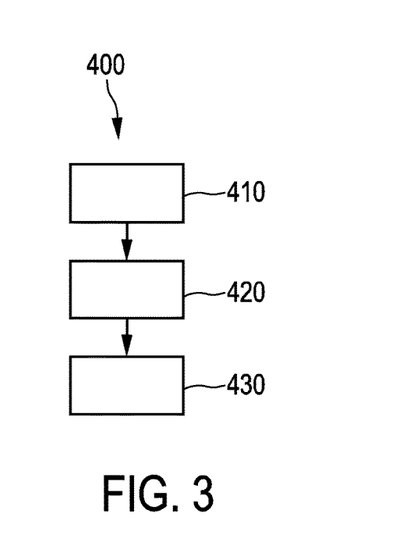
FIG. 3 shows schematically and exemplarily an embodiment of a method of providing at least one virtual marking.

FIG. 3 shows schematically and exemplarily an embodiment of a method 400 of providing at least one virtual marking for the optical-shape-sensing-enabled interventional device 125. A step 410 refers to providing optical shape sensing data for at least a part of the interventional device. A step 420 refers to providing reconstructed shape data for the interventional device based on the optical shape sensing data. A step 430 refers to providing at least one virtual marking based on said reconstructed shape data.

Figure 4:
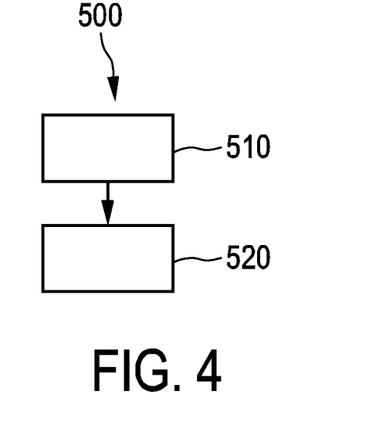
FIG. 4 shows schematically and exemplarily an embodiment of a processing method.

FIG. 4 shows schematically and exemplarily an embodiment of a processing method 500. A step 510 refers to providing reconstructed shape data of the interventional device 125, wherein interventional device 125 is configured for being arranged within a subject. A step 520 refers to providing at least one virtual marking based on said reconstructed shape data.

Figure 5:
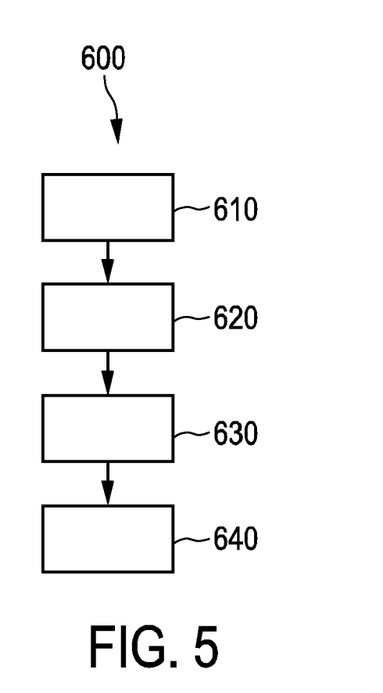
FIG. 5 shows schematically and exemplarily an embodiment of an imaging method.

FIG. 5 shows schematically and exemplarily an embodiment of an imaging method 600 for imaging the interventional device 100. A step 610 refers to generating a region of interest representation representing a region of interest within the subject. A step 620 refers to arranging the optical-shape-sensing-enabled interventional device 125 within the subject and to providing at least one virtual marking in accordance with method 400. A step 630 refers to registering said at least one virtual marking with said region of interest representation. A step 640 refers to displaying said at least one virtual marking together with said region of interest representation.

Optical shape sensing technology may e.g. provide a three-dimensional shape of an optical fiber. By integrating such a fiber in interventional devices, the shape of the device can be known.

Figure 6:
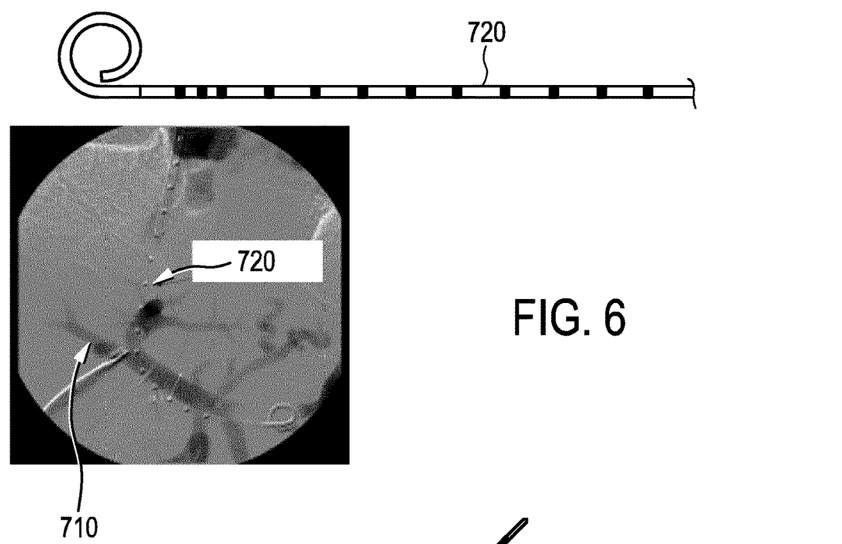
FIG. 6 shows a pigtail catheter with radiopaque markers.
Figure 7:
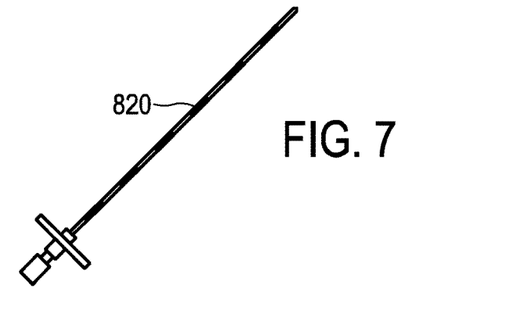
FIG. 7 shows an epidural needle with depth markings.
Figure 8:
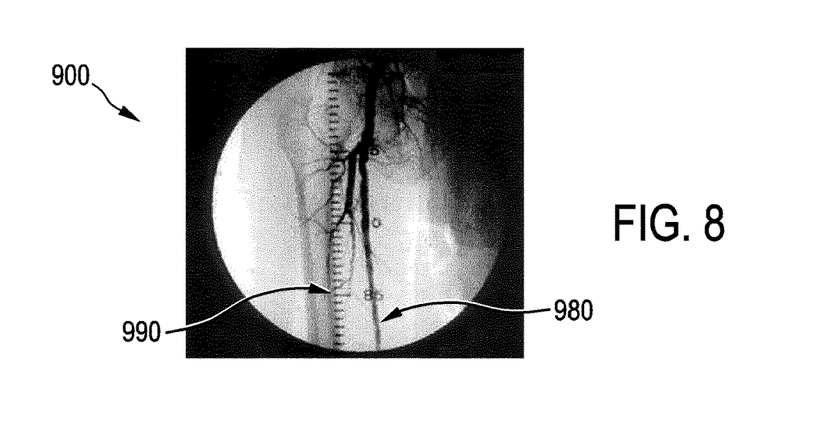
FIG. 8 shows an example of a radiopaque ruler.

In conventional interventional devices, measuring distances inside a patient is performed with radiopaque rulers 990 overlaying x-ray images 900 to determine the dimensions of e.g. blood vessels 980 (as shown e.g. in FIG. 8) and devices with radiopaque markers (as shown e.g. in FIGS. 6 and 7). US 2010/0318182 A1 describes radiopaque markers placed at known relative distances. U.S. Pat. No. 5,860,923 A describes radiopaque markers indicating the start and end of a path to be measured with some kind of visible ruler outside the patient. However, these are often devices dedicated for measurements and have less or no properties for easy navigation or stent placement.

Due to foreshortening and the inverse perspective of x-ray imaging, it is difficult to do reliable measurements based on x-ray imaging alone. Namely, the scale on a radiopaque ruler is only valid on the plane perpendicular to the view direction at the depth of the ruler. Therefore, physicians often use a calibrated device, such as a pigtail catheter 720 (as shown in FIG. 6) introduced into a vessel 710, or a calibrated epidural needle 820 (as shown in FIG. 7). The radiopaque markers are at a known relative distance, allowing the user to do 3D length measurements by counting the markers and estimating the length. The main problem is that each time a user wants to do a measurement, a dedicated calibrated device needs to be used, because not every device has these markings. In endovascular procedures, when a guide wire is in place, a calibrated device can be slid over it, but it requires some work replacing devices. The present invention turns of OSS-enabled devices into calibrated devices, thereby eliminating the need for dedicated calibrated devices in cases where OSS-enabled devices are used, hence improving the workflow and reducing costs.

Figure 9:
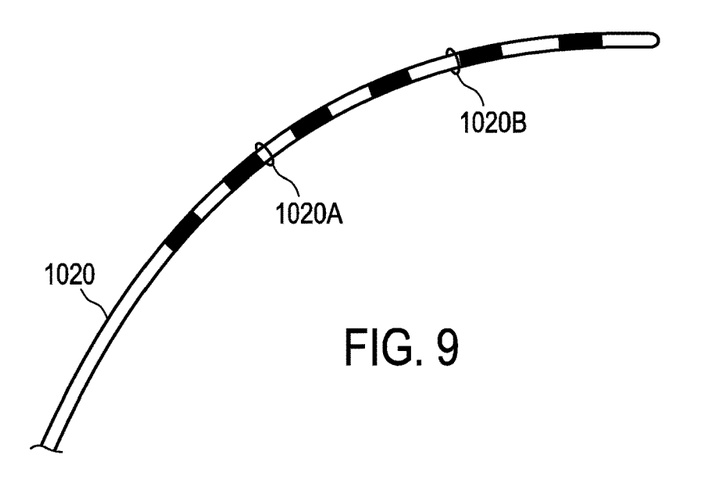
FIG. 9 shows an example of markings on a virtual device.

The present invention is based on the insight that any OSS-enabled device can provide information about distances. The device's reconstructed shape can provide a visualization of virtual markers, where the virtual markers may provide the same functionality to radiopaque markers of conventional calibrated devices. With virtual markings based on performing optical shape sensing, it is even possible to provide a more accurate scale. This is because radiopaque markers have a certain thickness leaving the precise length between two positions to be estimated by the user. The virtual markings may comprise actual 3D points, so the distances between these points are very accurate. Furthermore, as illustrated e.g. in FIG. 9, the visualization of virtual markings 1020A, 1020B for an interventional device 1020 can be improved, e.g. by changing the graphics.

The reconstructed shape is calculated in a known space (for example millimeter space). Therefore, 3D distances (i.e., along a straight line or along the reconstructed shape) can be calculated in this space by using the points of the reconstructed shape. If it is desired to use the present invention for doing measurements in pre- or intra-procedural data, it is preferable to place the reconstructed shape in the context of, i.e. register with, the pre- or intraprocedural data.

An improved user experience may be achieved by labeling the virtual markings so that the user does not need to count each virtual marking. In an embodiment, the virtual markers can be toggled on and off, such that a view is less crowded. This is particularly useful when the user is not measuring. The scale (unit size) of the markings can be adjusted to the preference of the user (centimeters or millimeters) or to the standard in the geographical area (metric or imperial system). One advantage of being able to do so is that the physical device does not need to be changed. In another embodiment, the scale can be made dependent on how far the user zooms in.

Figure 10:
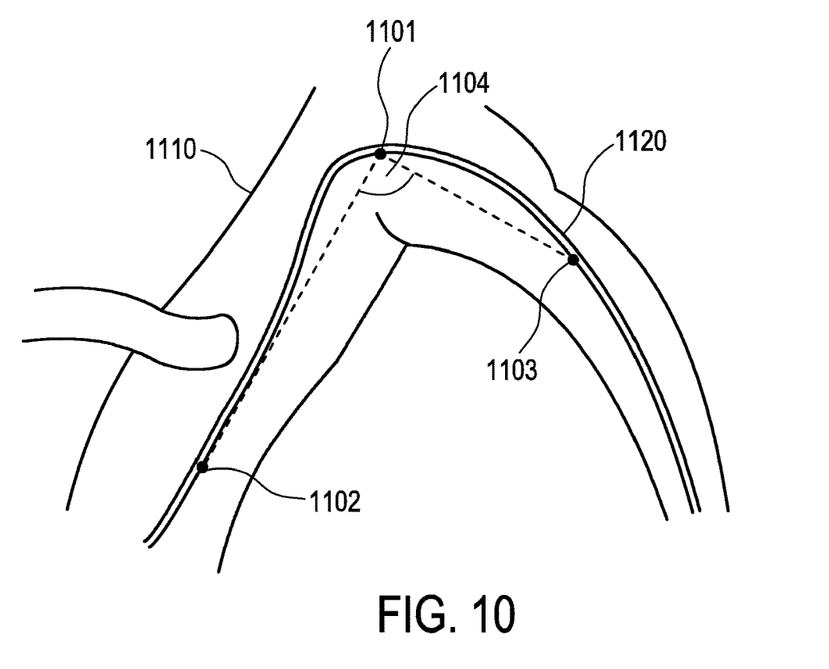
FIG. 10 shows an example of performing angle measurements using virtual markings on an interventional the device.

As illustrated in FIG. 10, live angle measurements can be done by selecting three virtual markings or three 3D positions 1101, 1102, 1103 on an interventional device 1120 within a subject 1110. Without the 3D shape as proposed by the present invention, an angle 1104 can be calculated on the pre-op volume, obtained from e.g. CT or MR, but this may be inaccurate due to distortion of anatomy. Angle 1104 may further be calculated on a volume, obtained from an intra-procedural rotational X-ray scan, but this requires extra x-ray exposure and maybe additional (toxic) contrast agent. Conventional angle measurements performed directly in x-ray images are less accurate, because of foreshortening and inverse projection of x-ray. Furthermore, only in-plane angles can be determined from an x-ray image. By using the 3D shape as proposed by the present invention, these drawbacks may be overcome.

A user may select points using a live shape, or a recorded (static) shape.

Some angles might be calculated automatically, for example by using fixed points or looking at the curvature of the shape. Angle measurements can also be done by selecting two times two 3D positions on the device. The point pairs define two lines between which the angle can be calculated.

Figure 11:
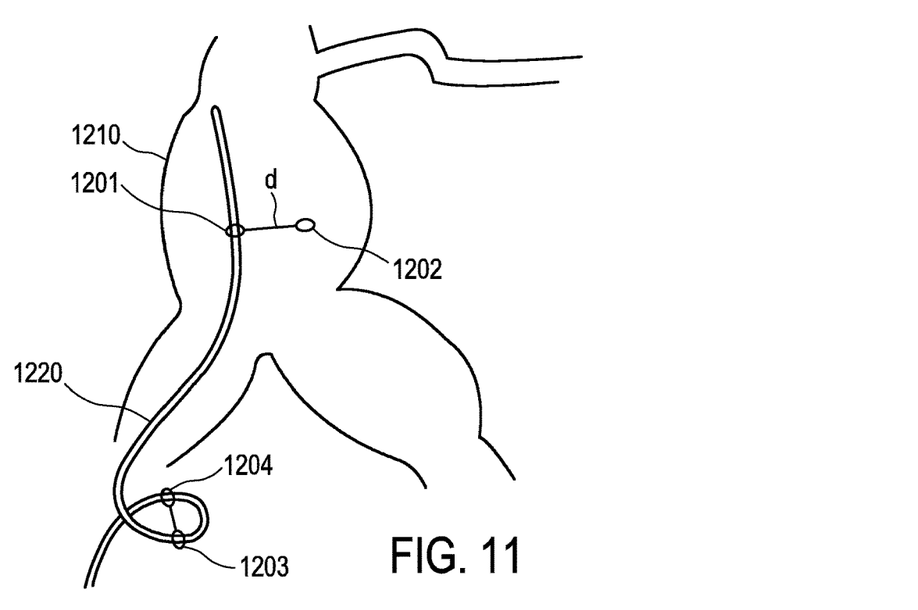
FIG. 11 shows an example of performing a distance measurement between two virtual markings on an interventional device and an example of determining the shortest distance between a 3D point and the interventional device.

As illustrated by FIG. 11, a distance between points 1203, 1204 on interventional device 1220 within subject 1210 can be calculated and shown to the user (so not only the length along the device but also the Euclidean shortest distance between two points). Also, a distance d between virtual marking 1201 and a pre-defined location 1202 within subject 1210 may be determined. The length of the path that the tip (or any other particular point) of the device traveled during a certain period of time might be useful for the user. For this, not the entire shape of the device needs to be known, but only the position of one point on the device over time. Hence, this benefit may not only apply to OSS, but also to other modalities that can track a point over time.

Measurements using multiple OSS-enabled interventional devices may be carried out as follows: If one device is in the lumen of the other, for example a guide wire inside a catheter, the distance along the device from one distal tip to the distal tip of the other device can be calculated and shown to the user. It can give the user information about how far a device can be inserted before the tips reach each other. It can also be used to do quick length measurements by holding each tip at one end of a lesion so that one may directly determine the length. Further, a live distance between (user defined) fixed virtual markings on multiple devices may be determined, independent of whether both interventional devices are inside each other or not.

Figure 12:
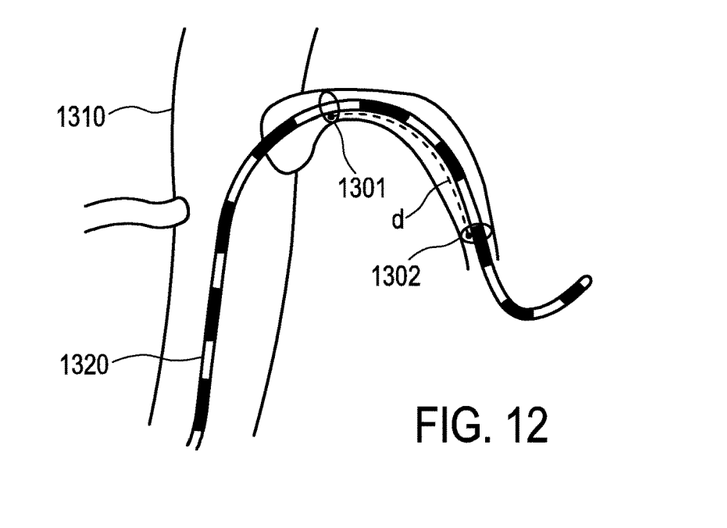
FIG. 12 shows an example of performing a distance measurement along the interventional device.

Measurements using a registered 3D volume or 3D anatomical landmarks may involve the following: Determining a distance between a defined 3D location (landmark) and a fixed position on a device; determining the shortest distance between a defined 3D location (landmark) 1202 and interventional device 1220 (see FIG. 11). One way to do this is to identify the virtual marking 1201 on interventional device 1220, which is closest to 3D location (landmark) 1202 and then to determine the distance d between virtual marking 1201 and 3D location (landmark) 1202. Measurements using a registered 3D volume or 3D anatomical landmarks may further involve determining a shortest/average/maximum distance to a center line of a segmented vessel. Measurements using a registered 3D volume or 3D anatomical landmarks may further involve determining a distance to (segmented) anatomical features such as calcification, Ostia and/or vessel wall. Measurements using a registered 3D volume or 3D anatomical landmarks may further involve determining a distance (either Euclidean or along the device) to an intersection points with a plane (for example defined by a ring). This is illustrated by FIG. 12 where interventional device 1320 is introduced into subject 1310. A distance d between virtual markings 1301, 1302 is determined by identifying intersection points with two planes (illustrated as rings in FIG. 12) and then determining distance d along interventional device 1320.

A device can determine a cut plane of a volume. In this plane, 2D measurements can be done, like area (of vessels outline) and shortest distance to a vessel wall. Positions on a shape, for example the tip or a position clicked by the user, can be fixated and stored as 3D landmarks. The user may place 2D landmarks on x-ray images and use those for distance measurements in combination with a device (shortest distance, or distance to a point on the shape). The 2D landmark may describe e.g. a line in 3D from the source of the x-ray system to the detector. The distance is not the exact distance between the anatomical feature tagged with the 2D landmark and the device, because it is not known where the anatomical feature is positioned on the line.

There are different options to provide the user with a distance which is some sort of estimation of the real distance: The position on the line may have the same depth as the position on the device, so the measurement is in the plane perpendicular to the x-ray image. The position may further lie on the line in the plane, which goes through the iso-center and is perpendicular to the x-ray image. The user can determine the depth, for example with help of an image made from a different angle.

Selected 3D points as described in the embodiments above (such as on device, on 3D volume or on x-ray) can be used to define a 3D virtual ruler instead of only providing the 3D distance between the points. In this way distance information of content visible in the X-ray could be measured more accurately. In a similar way, three 3D points can define a 3D plane, which can be used for a ruler grid, such that measurements can be done in this plane. The position and shape of the device can provide a suggestion for a viewing position (such as a table and C-arm position). The user can define three points on the shape that describe a view plane. A plane can be automatically calculated based on certain points, curvature, direction of certain points or a combination of all these.

Figure 13:
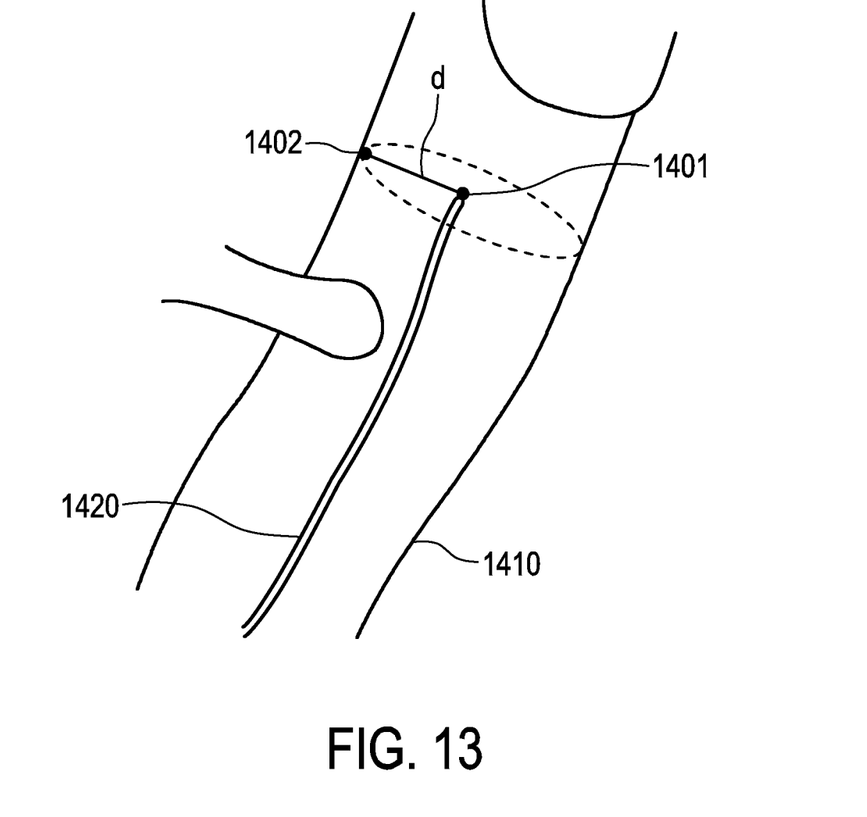
FIG. 13 shows an example of determining an area and shortest distance to a vessel wall based on a segmented CT.

A further embodiment is illustrated by FIG. 13, where interventional device 1420 is introduced into subject 1410, such as, e.g., a blood vessel. A virtual marking 1401 is provided at the tip of interventional device 1420. The present invention may then be used to determine the distance d (preferably: the shortest distance) to the vessel wall 1402.

Figure 14:
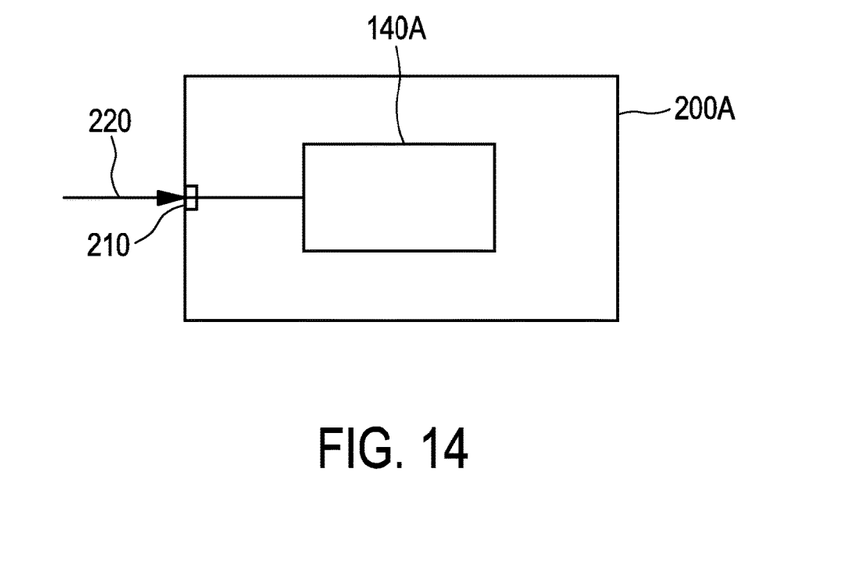
FIG. 14 shows schematically and exemplarily a further embodiment of a processing system.

FIG. 14 shows schematically and exemplarily a further embodiment of a processing system 200A. The processing apparatus 200A comprises: a receiving unit 210 that is configured for receiving reconstructed shape data 220 of interventional device 100. Receiving unit 210 may comprise an input unit. The processing apparatus 200A further comprises a virtual marking provider unit 140A that is configured to provide at least one virtual marking based on said reconstructed shape data 220.

An example application of the invention is any (medical and non-medical) application comprising OSS-enabled devices.

All arrangements of the processing apparatus can be used with the optical-shape-sensing-enabled interventional device and/or with the imaging apparatus in accordance with the invention.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like distance and angle measurements etc. performed by one or several units or devices can be performed by any other number of units or devices. For example, the determination of a distance between two virtual markings can be performed by a single unit or by any other number of different units. The control of the processing apparatus in accordance with the above described processing method can be implemented as program code means of a computer program and/or as dedicated hardware. The control of the imaging apparatus in accordance with the above described imaging method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The present invention relates to a processing system that is arranged to cooperate with an optical-shape-sensing-enabled interventional device, such as a catheter comprising an optical fiber. A reconstructed shape data providing unit provides reconstructed shape data for the interventional device. A virtual marking provider unit provides at least one virtual marking based on the reconstructed shape data, for example as overlay to an x-ray image. The present invention thus turns any OSS-enabled device into a calibrated device, suitable for all kinds of live 3D measurements.

The invention claimed is:

1. A processing system arranged to cooperate with an optical-shape-sensing-enabled elongated interventional device, comprising:
   a reconstructed shape data providing unit that is configured for providing reconstructed shape data of said interventional device based on optical shape sensing (OSS) data; and
   a virtual marking provider unit that is configured to provide virtual markings at a known relative distance based on said reconstructed shape data for turning the interventional device into a calibrated device.

2. The processing system of claim 1,
   wherein the processing system further comprises a region of interest representation unit that is configured for generating a region of interest representation representing a region of interest within a subject; and
   a registration unit that is configured to register said virtual markings when said interventional device is arranged within said subject with said region of interest representation.

3. The processing system of claim 1,
   wherein said processing system is configured to determine a distance between at least one virtual marking and a reference point.

4. The processing system of claim 1,
   wherein said virtual marking provider unit is configured to provide a first and a second virtual marking, wherein said processing system is configured to determine a distance (d) between said first and second virtual markings.

5. The processing system of claim 1,
   wherein said virtual marking provider unit is configured to provide a first, second, and third virtual markings, wherein said processing system is further configured to determine at least one angle formed by said first, second, and third virtual markings.

6. The processing system of claim 1,
   wherein said virtual marking provider unit is configured to provide a first pair and a second pair of virtual markings, wherein said first pair and said second pair are forming respective first and second straight lines, and wherein said processing system is further configured to determine at least one angle formed by said first and second straight lines.

7. An imaging system for imaging an elongated interventional device within a subject, wherein said imaging system comprises:
   the processing system as defined in claim 1; and
   a display unit that is configured to display said marking.

8. The imaging system of claim 7,
   wherein said processing system further comprises a region of interest representation unit that is configured for generating a region of interest representation representing a region of interest within said subject; and
   a registration unit that is configured to register said at least one virtual marking when said interventional device is arranged within said subject with said region of interest representation,
   wherein said display unit is configured to display said virtual marking together with said region of interest representation.

9. The imaging system of claim 7,
   wherein said display unit is configured to display a three-dimensional virtual ruler.

10. A processing method comprising:
    providing reconstructed shape data of an optical-shape-sensing-enabled elongated interventional device, wherein said interventional device is configured for being arranged within a subject; and
    providing virtual markings at a known relative distance based on said reconstructed shape data for turning the interventional device into a calibrated device.

11. A non-transitory computer readable medium, having stored thereon a computer program for providing at least one virtual marking for an optical-shape-sensing-enabled elongated interventional device, the computer program comprising program code for causing a processing system as defined in claim 1 to carry out a processing method, comprising:
    providing reconstructed shape data of an optical-shape-sensing-enabled elongated interventional device, wherein said interventional device is configured for being arranged within a subject; and
    providing virtual markings at a known relative distance based on said reconstructed shape data for turning the interventional device into a calibrated device.

* * * * *